(12) United States Patent
Ramsey et al.

(10) Patent No.: US 6,231,737 B1
(45) Date of Patent: May 15, 2001

(54) MATERIAL TRANSPORT METHOD AND APPARATUS

(75) Inventors: J. Michael Ramsey; Roswitha S. Ramsey, both of Knoxville, TN (US)

(73) Assignee: UT-Battelle, LLC, Oak Ridge, TN (US)

(*) Notice: Subject to any disclaimer, the term of this patent is extended or adjusted under 35 U.S.C. 154(b) by 0 days.

(21) Appl. No.: 09/440,892

(22) Filed: Nov. 16, 1999

Related U.S. Application Data

(62) Division of application No. 08/726,355, filed on Oct. 4, 1996, now Pat. No. 6,110,343.

(51) Int. Cl.$^7$ .......................... G01N 27/26; G01N 27/447
(52) U.S. Cl. .......................... 204/451; 204/450; 204/600; 204/601
(58) Field of Search .................................. 204/600, 601, 204/602, 603, 604, 605, 450, 451, 452, 453, 454, 455

(56) References Cited

U.S. PATENT DOCUMENTS

| | | | |
|---|---|---|---|
| Re. 34,757 | * 10/1994 | Smith et al. | 204/603 |
| 4,908,112 | * 3/1990 | Pace | 204/601 X |
| 5,015,350 | * 5/1991 | Wiktorowicz | 204/454 |
| 5,073,239 | 12/1991 | Hjerten | 204/453 |
| 5,092,973 | 3/1992 | Zare et al. | 204/452 |
| 5,110,424 | * 5/1992 | Chin | 204/451 |
| 5,110,431 | 5/1992 | Moring | 204/451 |
| 5,132,012 | 7/1992 | Miura et al. | 210/198.2 |
| 5,141,621 | 8/1992 | Zare et al. | 204/453 |
| 5,180,480 | 1/1993 | Manz | 204/644 |
| 5,250,263 | 10/1993 | Manz | 422/81 |
| 5,296,114 | 3/1994 | Manz | 204/451 |
| 5,376,252 | 12/1994 | Ekström et al. | 204/603 |
| 5,480,614 | * 1/1996 | Kamahori | 422/70 |
| 5,605,613 | * 2/1997 | Shieh | 204/451 |
| 5,630,924 | * 5/1997 | Fuchs et al. | 204/601 |
| 5,705,813 | * 1/1998 | Apffel et al. | 250/288 |
| 5,872,010 | * 2/1999 | Karser et al. | 436/173 |

FOREIGN PATENT DOCUMENTS

| | | |
|---|---|---|
| 0 356 160 A2 | 2/1990 | (EP) . |
| 0 620 432 A1 | 4/1993 | (EP) . |
| 620432 | * 10/1994 | (EP) . |
| 620432 A1 | * 10/1994 | (EP) . |
| 2 191 110 | 12/1987 | (GB) . |

OTHER PUBLICATIONS

Stephen C. Jacobson et al, "Effects of Injection Schemes and Column Geometry on the Performance of Microchip Electrophoresis Devices" Analytical Chemistry, vol. 66, No. 7 pp. 1107–1113, Apr. 1, 1994.*

(List continued on next page.)

*Primary Examiner*—Jeffrey Snay
*Assistant Examiner*—John S. Starsiak, Jr.
(74) *Attorney, Agent, or Firm*—Dann, Dorfman, Herrell and Skillman, P.C.

(57) ABSTRACT

An electrospray apparatus uses a microchannel formed in a microchip. Fluid is pumped through the channel to an outlet orifice using either hydraulic or electrokinetic means. An electrospray is generated by establishing a sufficient potential difference between the fluid at the outlet orifice and a target electrode spaced from the outlet orifice. Electrokinetic pumping is also utilized to provide additional benefits to microchip devices.

10 Claims, 12 Drawing Sheets

OTHER PUBLICATIONS

Science . vol. 261 . Aug. 13, 1993 entitled: Micromachining a Miniaturized Capillary Electrophoresis–Based Chemical Analysis System on a Chip, by D. Jed Harrison, Karl Fluri, Kurt Seiler, Zhonghui Fan, Carlo S. Effenhauser, and Andreas Manz.

D. Jed Harrison, Andreas Manz, Zhonghui Fan, Hans Lüdi, and H. Michael Widmer, "Capillary Electrophoresis and Sample Injections Systems Integrated on a Planar Glass Chip" Analytical Chemistry, vol. 64, No. 17 (Sep. 1, 1992) 1926–1932.

Carlo S. Effenhauser, Andreas Manz, and H. Michael Widmer, "Glass Chips for High Speed Capillary Electrophoresis Separations with Submicrometer Plate Heights" Analytical Chemistry, vol. 65, No. 19 (Oct. 1, 1993) 2637–2642.

M. Deml, F. Foret, and P. Boček, "Electric Sample Splitter for Capillary Electrophoresis" Journal of Chromatography, 320 No month available (1985) 159–165.

* cited by examiner

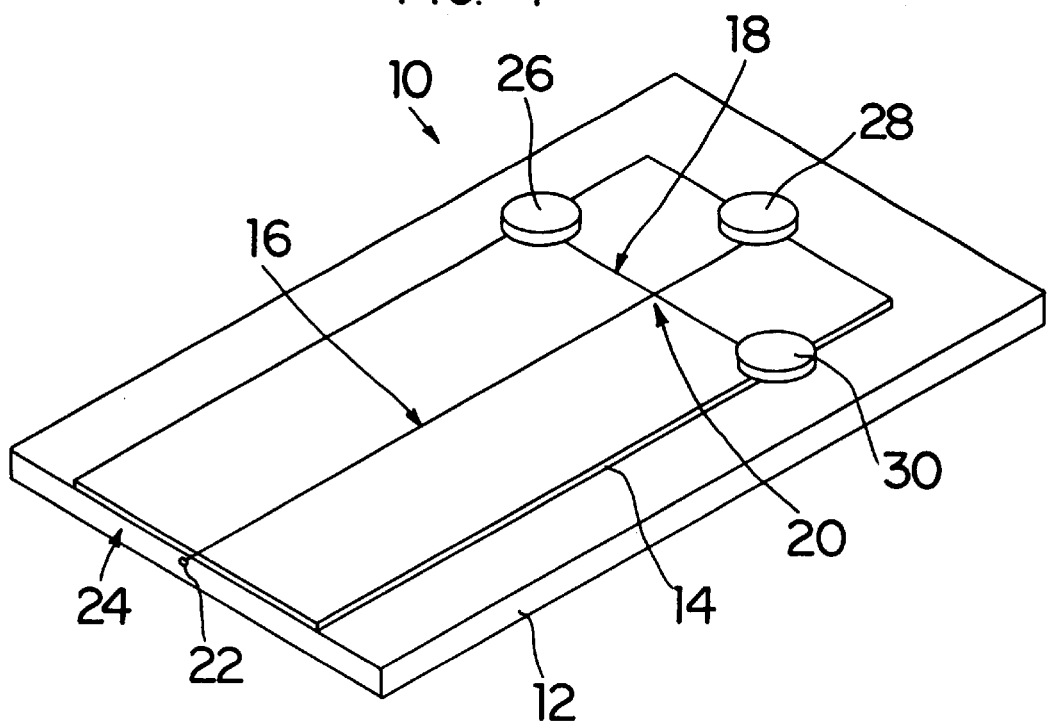
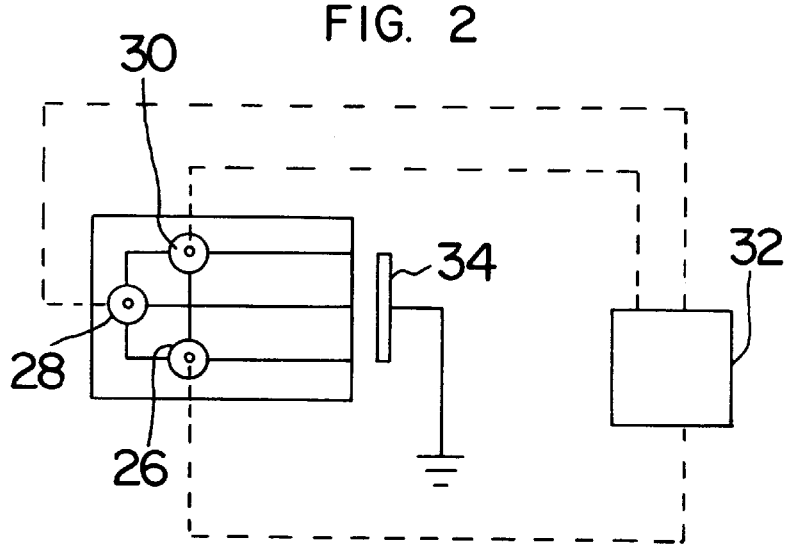

MATERIAL TRANSPORT METHOD AND APPARATUS

CROSS-REFERENCE TO RELATED APPLICATION

This application is a divisional application of U.S. Ser. No. 08/726,355, filed Oct. 4, 1996 (now U.S. Pat. No. 6,110,343).

This invention was made with Government support under contract DE-AC05-840R21400 to Lockheed Martin Energy Systems, Inc. and the Government has certain rights in this invention.

FIELD OF THE INVENTION

The present invention relates generally to the field of chemical analysis and testing and, more specifically, to methods for transporting materials processed on microchips to off-chip devices for further interrogation. A microchip generates an electrospray from solutions emerging from channels etched on planar substrates. Fluids are delivered through the channels using either hydraulic or electrically driven forces and are sprayed electrostatically from the terminus of the channel. An electrical potential difference of sufficient magnitude to generate the electrospray is applied between a location on the microchip and a conductor spaced from the terminus of the channel.

BACKGROUND OF THE INVENTION

Recently, miniaturized chemical instruments have been fabricated using micromachining techniques. These "microchip" devices have been used to perform liquid phase separations such as electrochromatography and electrophoresis and mixing of reagents in integrated microreactors for chemical reactions.

Among their many advantages, microchips allow increased speed of analysis and reduced reagent and sample consumption over conventional bench-scale instruments. In addition, integrated devices provide significant automation advantages as fluidic manipulations are computer controlled. These integrated devices are now being referred to as "lab on a chip" technologies, as the operations of a complete wet chemical laboratory could potentially be integrated.

Many chemical analysis tools that are used in modern laboratories are not presently miniaturized and many are not thought to be amenable to miniaturization in the immediate future. Although the microchip technology is quite powerful, there are situations where after processing on a microchip, further chemical interrogation is desired off of the microchip. A convenient way to transport fluids from microchips to other devices is to generate droplets that can be directed to specific locations for collection and/or analysis. Ink jet technologies are in wide spread use in printer products and are currently used to distribute liquid borne chemicals with spatial selectivity. Early ink jet formation methods included continuous stream ink jets, impulse ink jets, electrostatically generated ink jets. See, for example, R. D. Carnahan, and S. L. Hou, *IEEE Trans. Ind. Appl.*, IA-13, 95 (1977). The first two methods use acoustic energy to form droplets and the latter uses electrostatic forces. Most modern ink jet printers utilize thermal energy to form droplets where bubble formation in the ink essentially provides the acoustic driving force to launch a droplet. See, for example, R. A. Askeland, W. D. Childers, and W. R. Sperry, *Hewlett Packard Journal*, August, pg. 28 (1988). Charged droplets and even molecular ions can be generated from liquids using the technique called "electrospray."

Electrospray is often used as a method for generating gas phase ions from solution for subsequent mass spectral analysis. Electrospray ionization is a soft ionization technique whereby species that are ionic in solution are transferred to the gas phase. The sample solution is dispersed as an electrically-charged aerosol and following solvent evaporation and disintegration of the droplets into smaller droplets, gas-phase ions are eventually produced. In the past, electrospray ion sources have employed needles or capillary tubes for spraying ion sources.

Essentially no fragmentation accompanies the ionization process and multiply-charged ions are typically produced from high mass polymers such as peptides, proteins, DNA and various synthetic polymers. Thus, electrospray ionization mass spectrometry is an effective means to provide primary and secondary structural analysis of polymeric materials.

SUMMARY OF THE INVENTION

An object of the present invention is to provide a method and apparatus for electrospraying a material for analysis in which the speed of analysis in increased.

Another object of the present invention is to provide a method and apparatus for transporting material from microchips by generating droplets that are directed to a receiving substrate or device.

Another object of the present invention is to provide a method and apparatus for electrospraying a material for analysis in which the amount of reagent and sample consumption are reduced.

Another object of the present invention is to provide a method and apparatus for electrospraying a material for analysis which is cost effective to produce and relatively simple in construction.

Another object of the invention is to provide a method and apparatus for electrospraying which enables a material manipulated by a planar substrate to be electrosprayed directly to a receiving device which uses the material as a gas phase entity or collects the droplets.

These and other objects are achieved by providing a method of electrospraying a material which includes placing the material i n a channel of a microchip, and forming an electric field in the channel with sufficient magnitude and direction to cause the material to be sprayed from an outlet of the channel.

Other objects, advantages, and salient features of the invention will become apparent from the following detailed description, which taken in with the annexed drawings, discloses the preferred embodiment of the present invention.

BRIEF DESCRIPTION OF THE DRAWINGS

FIG. 1 is a schematic view of a glass microchip with micromachined channels used to generate electrospray according to the present invention;

FIG. 2 is a schematic view of the microchip of FIG. 1 with a voltage supply and grounded electrode;

DETAILED DESCRIPTION OF THE PREFERRED EMBODIMENT

Figure 3A:
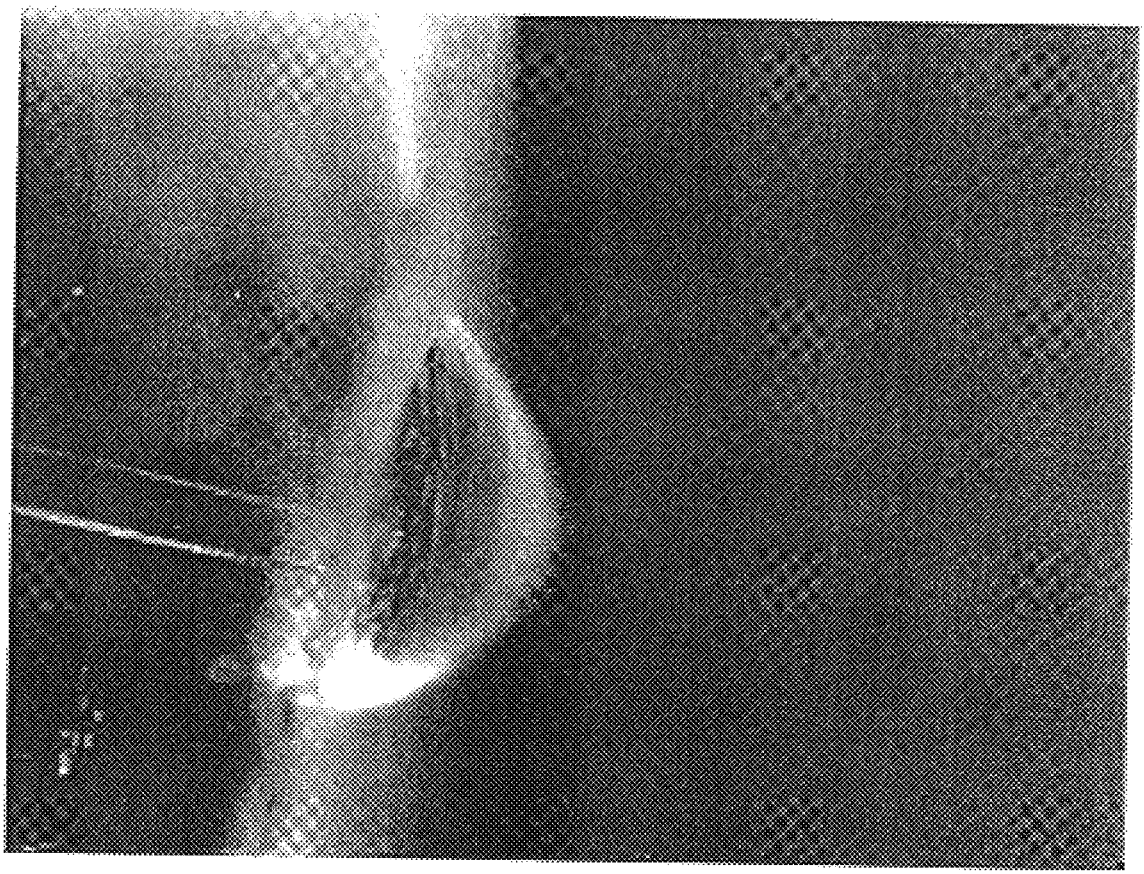
FIGS. 3A and 3B are photographs showing electrospraying according to the present invention.

Referring to FIG. 1, a microchip 10 includes a substrate 12 and a cover plate 14 bonded to the substrate 12. Both the substrate 12 and the cover plate 14 may be made of clear glass or other insulating materials such as quartz, fused silica, sapphire or plastics. One particular embodiment has the substrate 12 made from a standard glass microscope slide, and measures 40 mm in length and 25 mm in width.

The substrate 12 has a micromachined channel structure formed in the upper surface thereof, and including a first linear channel 16 and a transverse, intersecting linear channel 18. The two channels intersect at an area designated as the "intersection" 20. An exit port 22 is located at the end face 24 defined by the coplanar surfaces of the substrate 12 and cover plate 14.

Reservoirs 26, 28, and 30 are bonded to the substrate 12 over the terminal ends of the channels 16 and 18. Reservoirs 26 and 28 can be used for buffer or sample material, and reservoir 30 is for sample waste.

The microchip 10 is fabricated using standard procedures described in the literature. First the channels 16 and 18 are micromachined into the substrate surface using photolithographic patterning and wet chemical etching. Some typical channel dimensions are ≈60 μm wide by ≈10 μm deep. The cover plate 14 is direct bonded over the open channel structure to form closed channels. The small fluid reservoirs 26, 28, and 30 (where the channels exit from underneath the cover plate) allow fluidic communication with the channels.

The port 22 is created by scoring and breaking *he fabricated chip. The exit end face 24 of the microchip can be polished and/or chemically modified to control the hydrophobicity of the surface. These treatments do not greatly effect the electrospray performance. Exit surface hydrophobicity can control spatial location of fluid emanating from the channel opening. It should also be possible to spray in a direction normal to the plane of the substrate and cover plate by creating an exit orifice in that plane.

Referring to FIG. 2, electrical potentials are applied to the various reservoirs 26, 28, and 30 through a platinum wire inserted into the solutions contained in the reservoirs, or through other conducting material contacting the solutions contained in the reservoirs, and connected to respective voltage sources or a voltage source 32 with plural outputs. An electric field for an electrospray can be established by placing an electrode 34 near the exit port 22 and creating a potential difference between the electrode and the solution in the channel forming the exit orifice. The field strength for generating electrospray is typically several kV/cm and the desired polarity depends on the charge (negative or positive) of the ions to be generated. The electric contact to the spraying solution can be made in one of several ways, e.g., through one of the reservoirs 26, 28, 30, through a metal electrode formed on the end face 24, or through a side arm channel reservoir as described below.

For initial electrospray experiments, a voltage was applied to one of the buffer reservoirs relative to a grounded planar electrode placed in front of the channel opening. The distance between the electrode and the channel opening was typically 3–5 mm. The applied voltage was typically 3–6 kV. Electroosmotic flow due to electrospray currents is not sufficient, in general, to supply fluid to the channel opening for electrospray. Thus, a pressure of a few psig was applied to the three reservoirs to force fluid out the channel opening.

Figure 3B:
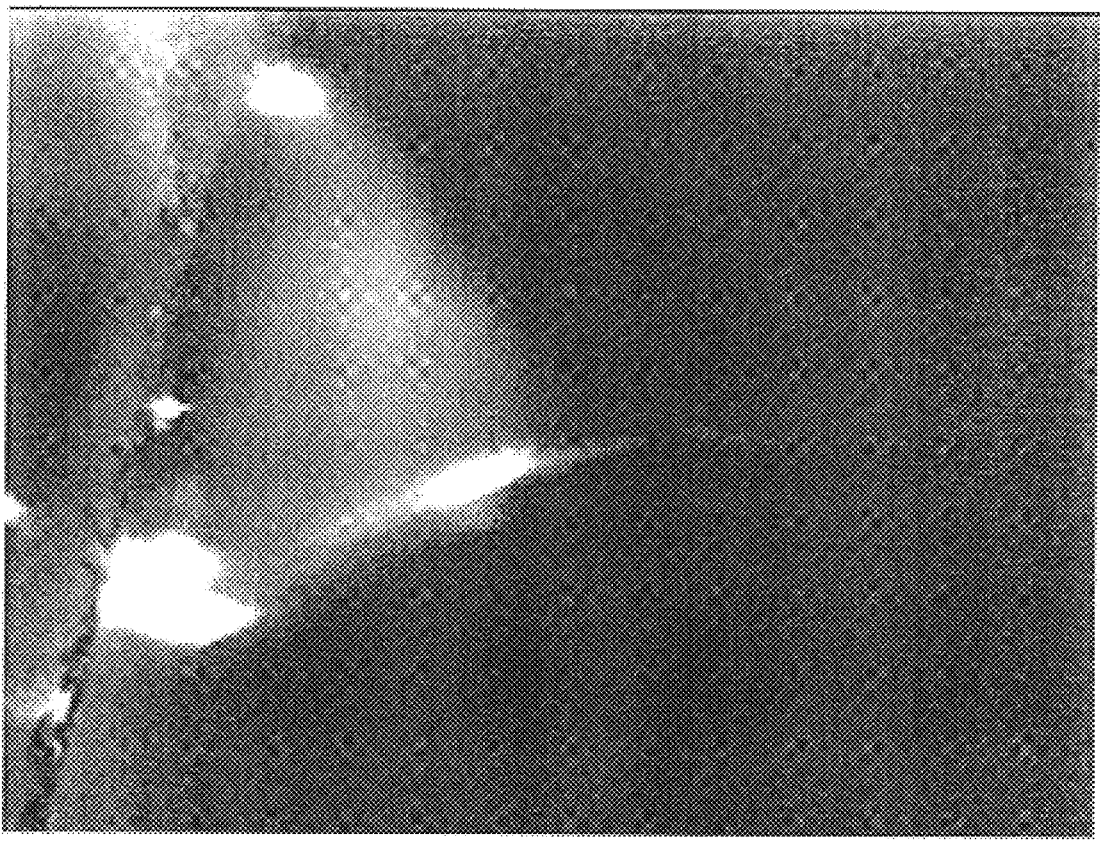

FIGS. 3A and 3B show a bead of solution at the channel opening without (3A) and with (3B) the electrospray field applied. A channel can be seen leading from left to right, terminating at the channel opening. Image 3A shows a hemispherical droplet as would normally be expected for a hydrophobic surface. Image 3B shows the droplet with the electrospray field applied. The droplet of buffer is pulled into a Taylor cone by the electric field between the solution droplet and the ground electrode or plate. A fine spray can be seen exiting from the tip of the Taylor cone as noted in FIG. 3B. Pure water and mixtures of water and methanol have been electrosprayed in this manner. Other solutions which can be electrosprayed include various buffers, solvents, and mixtures thereof.

Control over volumetric flow during electrospraying is critical to maintain a stable electrospray. If the flow rates are too low it may not be possible to establish the spray or it will be sporadic. Excessive flows will lead to formation of large droplets and poor ion signals will be obtained in the mass spectrometry. A method of generating fluid flow, in addition to pressure induced flow, is to use electroosmotically induced pressures as described below.

The velocity, v, of a fluid through a channel when driven by electroosmosis is given by Eq. 1

$$v = \frac{\epsilon \zeta E}{4\pi \eta} \quad \quad 1)$$

where E is the electric field strength, $\zeta$ is the zeta potential across the Stern layer at the channel-fluid interface, $\in$ is the dielectric constant of the fluid, and $\eta$ is the viscosity of the fluid at the interface. The steady state velocity of the fluid flow does not depend on the cross-sectional dimensions or geometry of the channel when all dimensions are much greater than the Stern layer thickness.

When an electric potential is applied across a channel of axially varying cross sectional area, the volumetric flow rate produced by electroosmotic pumping is constant along the channel axis. This can be confirmed from the following equations:
Flow rate, F $$F = vA(z) \qquad 2)$$

where $A(z)$ is the cross sectional area of the flow channel as a function of the axial distance z. Ohm's law for the channel can be written as, $$V = IR = I\rho \int_0^L \frac{dz}{A(z)} \qquad 3)$$

where V is the applied electric potential, I is the current, R the resistance, L the channel length and $\rho$ the resistivity of the buffer solution. The electric field strength, E, is given by the gradient of the electric potential along the channel axis.

$$E(z) = -\frac{dV}{dz} = I\frac{\rho}{A(z)} \qquad 4)$$

(The potential gradient along the z axis is assumed to have negative slope.) Combining equations 1), 4) and 2) gives, $$F = I\frac{\epsilon \zeta \rho}{4\pi\eta} \qquad 5)$$

The electric current, I, is a constant along the channel thus indicating that the flow rate, F, is independent of channel cross section, assuming that the channel interface and fluid are homoaeneous, i.e., the material constants $\epsilon$, $\zeta$, $\rho$, and $\eta$ are invariant throughout the channel structure.

For an interconnected channel structure, the electroosmotic flow will follow the current path as that path is the direction of the potential gradient or electric field, E.

Figure 4:
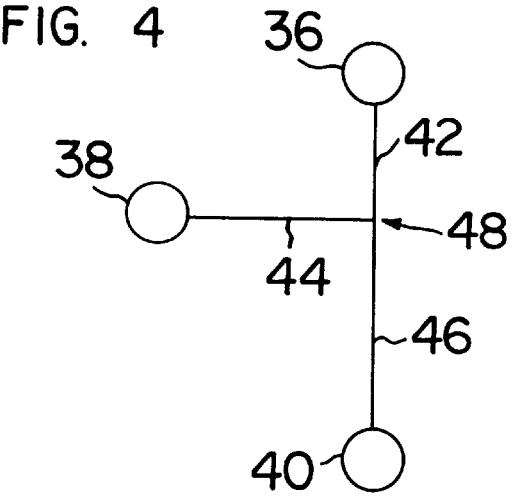
FIG. 4 is a schematic view of a three port microchip for demonstrating electroosmotic flow.

FIG. 4 is a schematic view of a three-port embodiment of the present invention. The three ports 36, 38, and 40 are interconnected by three channel sections 42, 44, and 46 intersecting at an intersection point 48.

The above analysis indicates that for a structure such as shown in FIG. 4, when an electric potential is applied between ports 36 and 38, there will be no flow from port 36 to port 40 irrespective of relative channel cross sections (again assuming dimensions are greater than the Stern layer). In the types of channel structures being discussed, the Reynolds numbers are typically much less than unity. Thus the viscous forces far exceed the inertial forces and there is no significant pressure generated at the intersection 48 to cause fluid flow from channel section 42 into channel section 46.

The above equations assume that the electroosmotic pumping is everywhere equivalent. Reduction of the electroosmotic fluid flow in channel section 44 relative to channel section 42 will generate an excess pressure in channel section 42, allowing pumping of fluid from port 36 to both ports 38 and 40.

The electroosmotic fluid flow in channel section 44 can be reduced relative to that in 42 by a number of methods including reducing the zeta potential, increasing the surface viscosity, or reducing dimensions below that of the Stern layer, within channel section 44. Assuming that the electroosmotic flow velocity has been reduced to zero in channel section 44, then the pressure generated at intersection 48 can be calculated using Equation (1) and the standard equations for pressure induced flow velocity with the velocities equated. For the channels used here the Hele-Shaw equation could be used or for circular cross section, the Poiseuille equation. The fluid flow in channel sections 44 and 46 can then be determined again using standard fluid mechanics with using the dimensions of the channels and the calculated pressure at point 48. The distribution of ions in channel sections 44 and 46 will require inclusion of electrophoretic forces in addition to bulk fluid flow.

Figure 5:
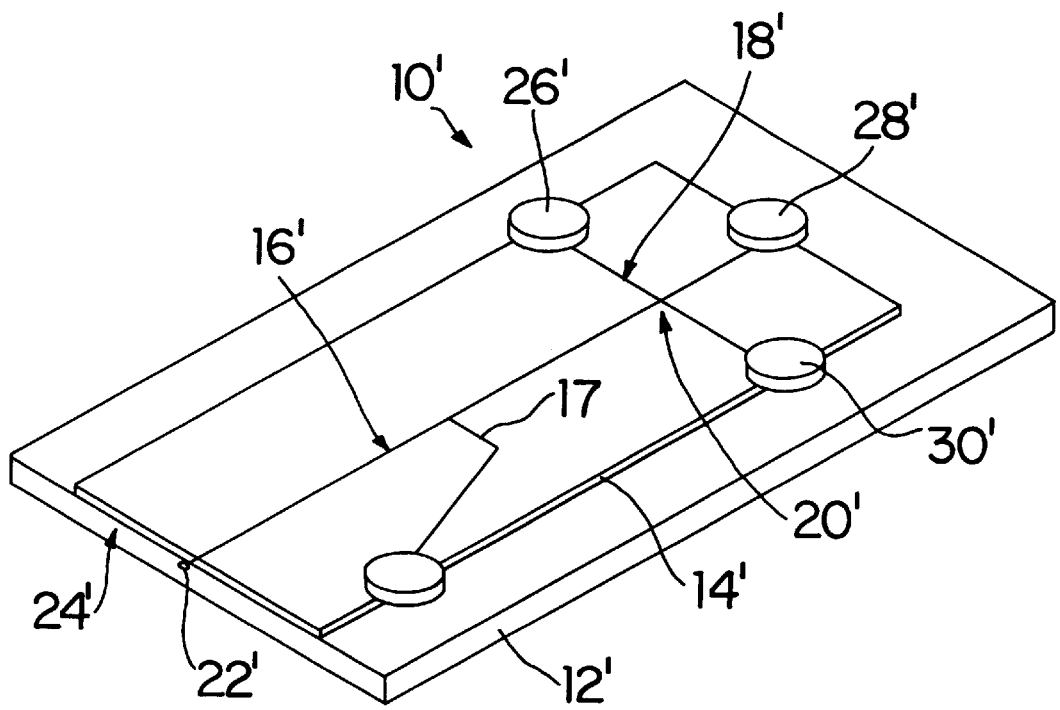
FIG. 5 is a perspective view of a microchip according to another embodiment of the present invention.

FIG. 5 shows a schematic of a microchip 10' which is a variation of the embodiment of FIG. 1. In FIG. 5, like parts have the same, but primed, reference numerals. The FIG. 5 embodiment was used to demonstrate the pumping principles described above. The chip layout is quite similar to that of FIG. 1 except for a side arm channel section 17 that branches off of the separation channel 16' below the injection intersection 20'.

Figure 6:
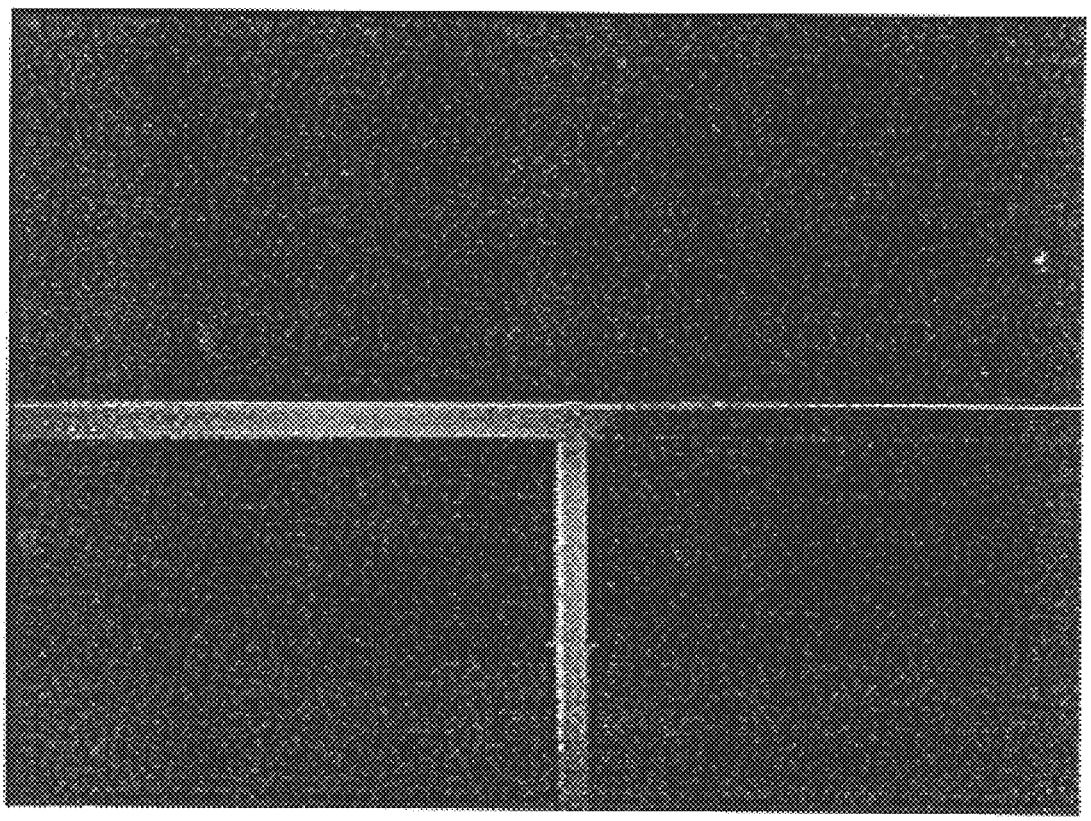
FIGS. 6–10 are CCD images and photomicrographs illustrating the electroosmotic pumping and electrospraying techniques of the present invention.

The channel dimensions are similar to those described above. FIG. 6 shows a fluorescence image of the side arm channel intersection with homogeneous channel conditions, i.e., all channel walls are native glass surfaces and should have uniform zeta potential. A positive potential is applied to the upper most reservoir connected to the central separation channel relative to the side arm reservoir. The upper reservoir contains water doped with Rhodamine B dye. The image area is illuminated with the 514 nm line of an argon-ion laser which excites the dye, while the CCD camera is viewing this area through an appropriate colored glass filter to observe the dye fluorescence.

In FIG. 6 the sample reservoir is to the left and the side arm is toward the bottom. The fluid flow is from left to right in the image. At the intersection a small amount of fluid can be seen to extend past the intersection, but the bulk fluid flow is toward the side arm reservoir. There is no flow of fluid to the right of the intersection. The spatial distribution of fluorescence is stationary with time. The narrow bright line seen in the image that extends to the right of the intersection is an artifact from specular reflections of the laser light from the channel facet.

Figure 7:
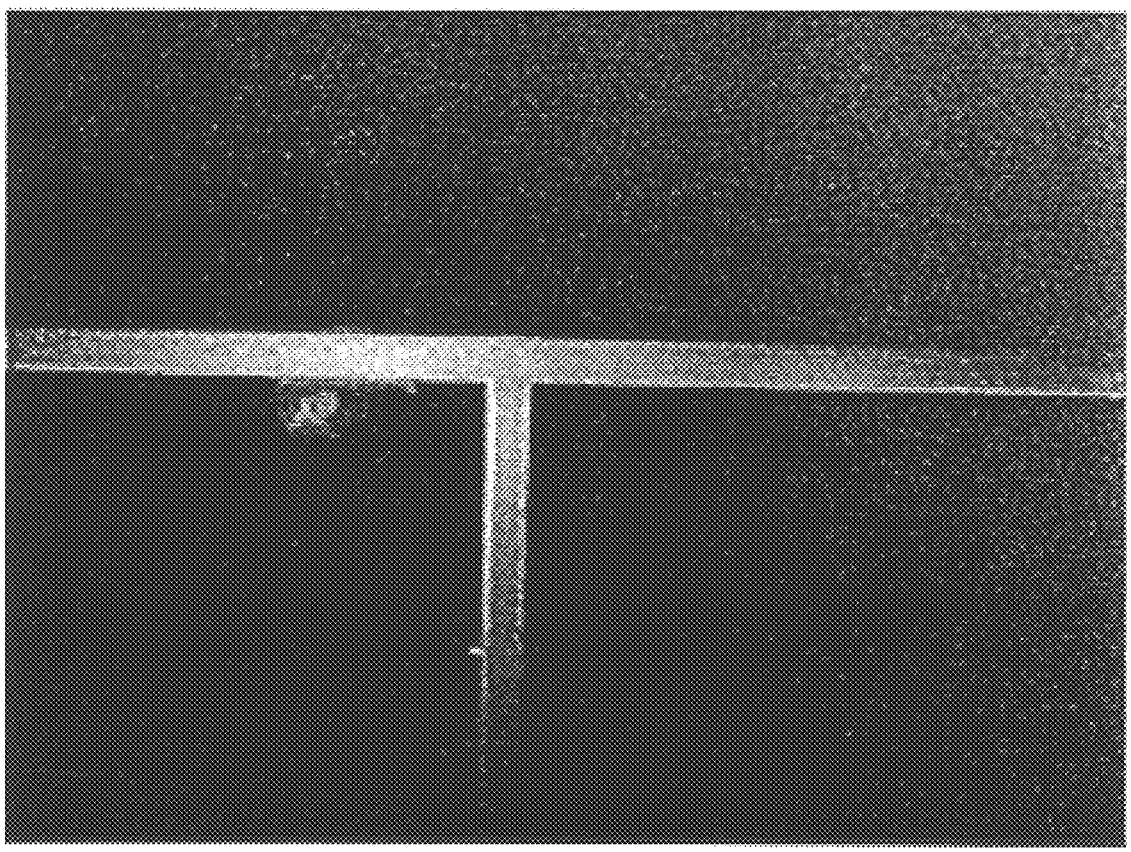

FIG. 7 shows a fluorescent image taken of the same chip intersection under the same experimental conditions except that the side arm channel and the channel between the intersection is and channel opening have been surface modified with linear polyacrylamide. The surface modification was performed using standard procedures and flowing the reagents between the side arm and channel opening only.

The linear polyacrylamide at the walls greatly increases the surface viscosity and thus reduces the electroosmotic flow, as indicated by Equation 1. It is clear in FIG. 7 that the dye solution propagates to the right of the intersection indicating the induced pressure generated at the intersection by the spatially inhomogeneous surface viscosity.

Figure 8:
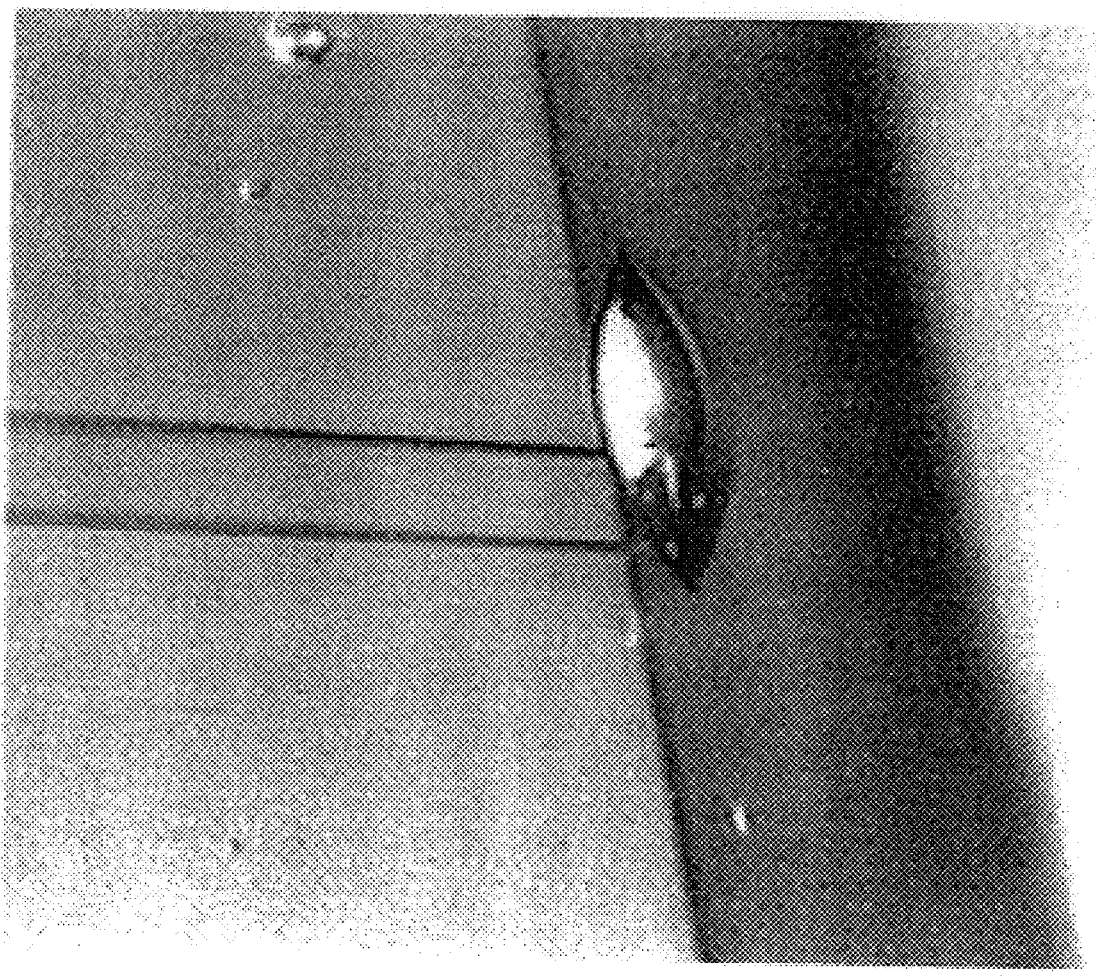
Figure 9:
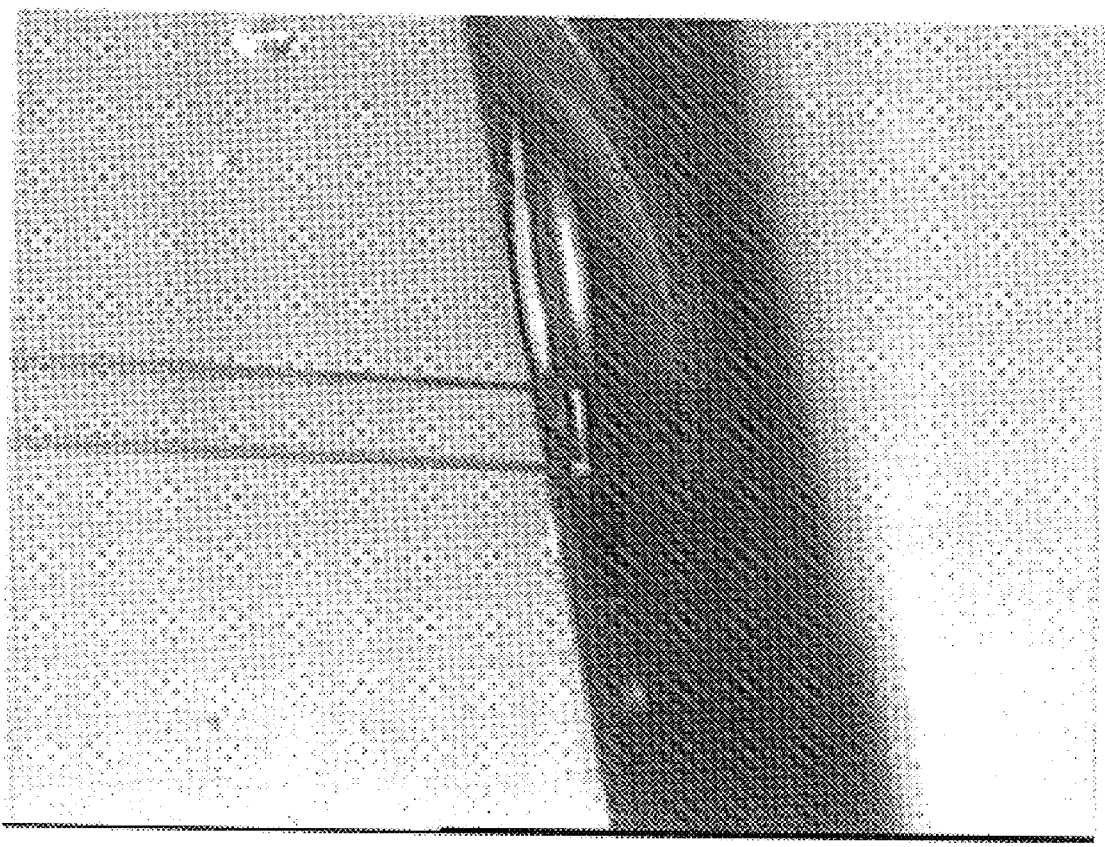

Evidence of fluid flow is also shown in FIGS. 8 and 9. In these white light images taken through a microscope, a drop of fluid has formed at the channel opening after application of the voltage as described above. The exit surface containing the channel opening is occasionally blotted with a sorbent wipe to remove any fluid. When the potential is applied a bead of fluid rapidly emerges. The images in FIGS.

8 and 9 are taken of the same chip separated by a short time interval. The size of the fluid droplet is clearly increasing.

Figure 10:
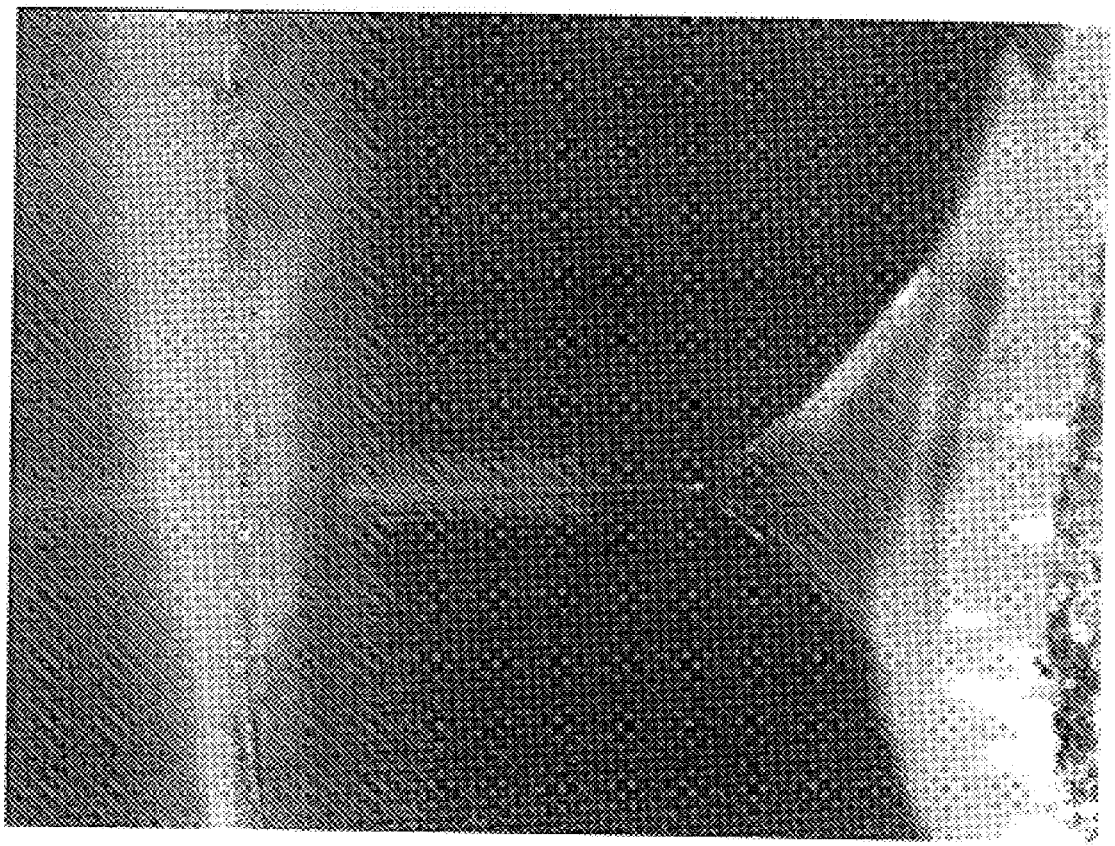

This electroosmotically driven fluid flow has been used to supply the fluid for electrospray from the chip. FIG. 10 shows a photomicrograph of electrospray generated from an aqueous solution containing 40% methanol. A voltage of 6 kV was applied to the top reservoir and 4 kV was applied to the side-arm reservoir, providing a 2 kV potential drop for electroosmotic pumping within the uncoated channel segment and ≈4 kV potential for electrospray formation. Alternatively, the side-arm may be held at ground potential and the counter electrode at the elevated voltages necessary to establish the electrospray. The chip was positioned 3 to 5 mm from the target plate which was held at ground potential. The target is evident on the left-hand side of the photograph. The electrical current has been measured on a grounded collector plate, which served as a counter-electrode, using an electrometer and ranges upward from 20 na depending upon the solvent and distance from the target. As above with the pressure induced flow, Taylor cone formation is clearly evident with an emanating electrospray plume. An argon-ion laser was used to illuminate the electrospray in the image shown in FIG. 10.

Figure 11:
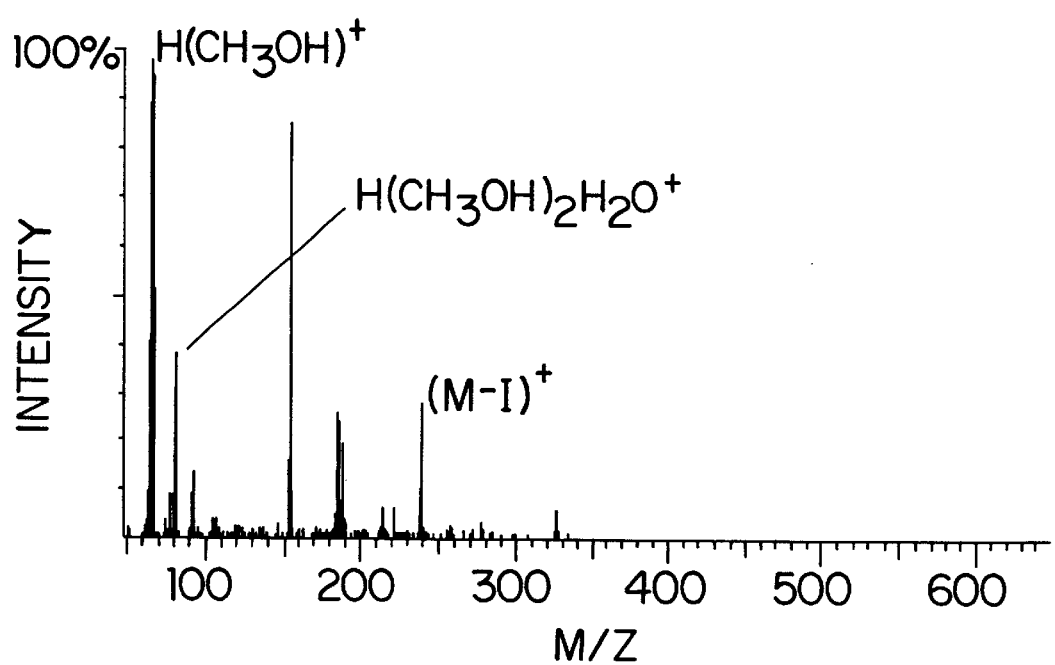
FIG. 11 is a mass spectrum obtained using the electrospraying techniques of the present invention.

A mass spectrum obtained from a 10 $\mu$M solution of tetrabutylammonium iodide (molecular weight=369) electrosprayed from the chip using electroosmotic pumping to deliver the analyte is shown in FIG. 11. Voltage conditions on the chip were the same as described above. The sample in 60/40 (v/v) water/methanol was continuously electrophoresed from the main channel to the exit where it was electrosprayed. The spectrum was obtained on a Finnigan-MAT quadrupole ion trap (San Jose, Calif.) modified for external ionization. The basic procedures used to sample gas-phase ions from an electrospray source and inject them into the ion trap for analysis have been published. In this experiment the ions were injected for 100 msec periods followed by a 300 msec delay before the mass analysis scan. Data were averaged over a 5 sec period. The tetrabutylammonium ion $(M-I)_+$ at mass/charge 242 is clearly evident as are some solvent cluster ions. Other major ions which are not identified may be due to fragmentation of the analyte.

Another common method for performing electrospray is called the "sheath" method, where a separation capillary tube is inserted inside a coaxial electrospray metal needle or capillary. A sheath fluid is pumped through the electrospray needle or capillary and thus makes contact with the separation buffer in the separation capillary. Thus, electrical connection of the separation potential to the separation capillary can be made through the sheath fluid.

Figure 12:
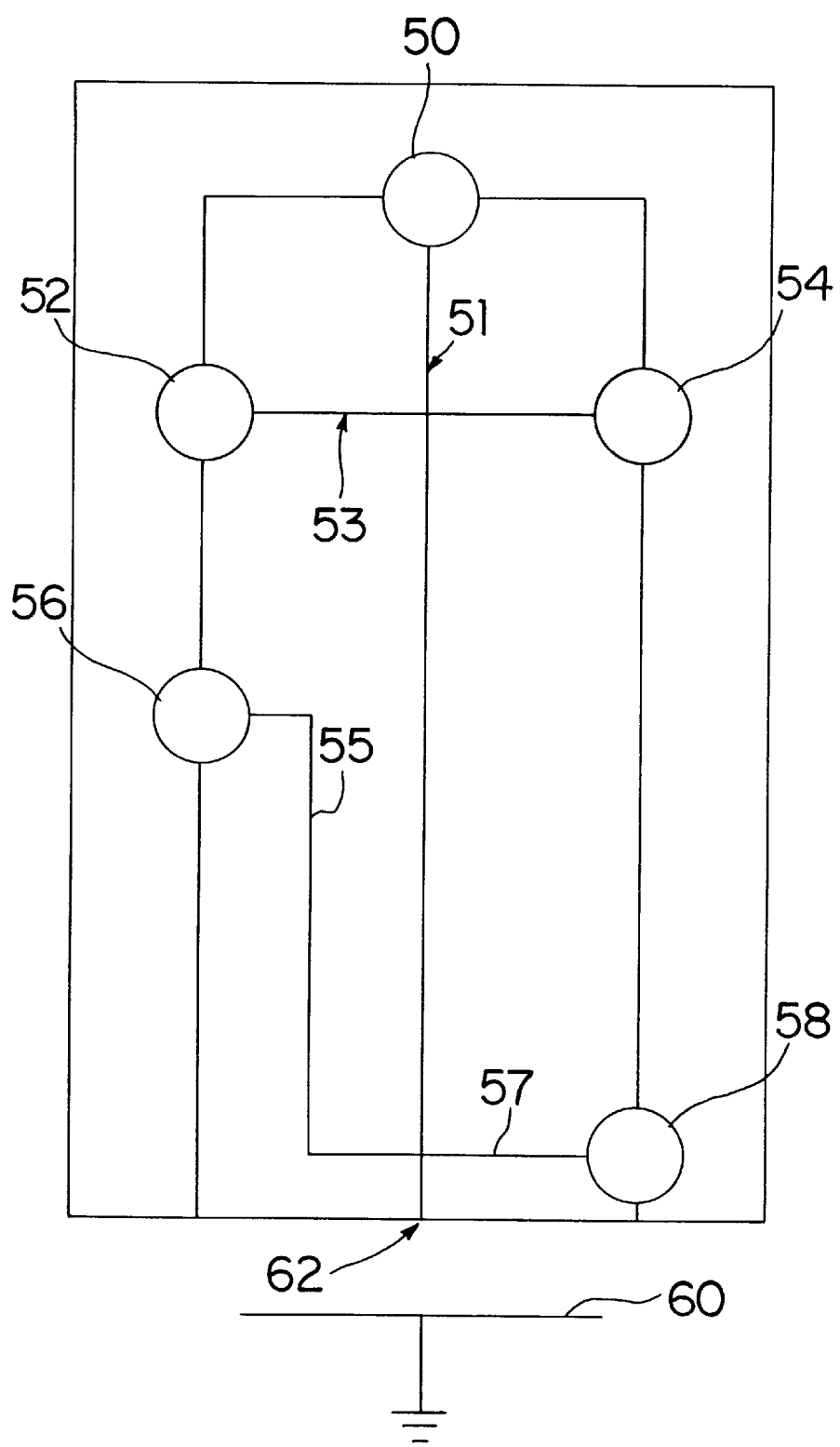
FIG. 12 is a top view of another channel architecture for an electrospray chip according to another embodiment of the present invention.

According to the present invention, this method of electrospray is implemented in a microchip format to provide a supplemental fluid for enhancing electrospray performance or for providing bulk fluid for electrospray when using coated separation channels that do not provide adequate electroosmotic flow. Referring to FIG. 12, reservoirs 50, 52, and 54 and associated channels 51 and 53 form the basis of an injection valve, which was disclosed in U.S. Ser. No. 08/283,769, filed Aug. 1, 1994, which is incorporated herein by reference. One of these channels would contain a sample to be analyzed. Reservoir 56 is connected to channel 51 by sheath channel 55 and generates an electroosmotic pressure using an appropriate electrospray buffer. Reservoir 58 is connected to the channel 51 by channel 57 and acts as the side arm channel described with reference to FIG. 5. That is, it provides an electrical potential lower than the other reservoirs for generating electric fields for separation in channel 51 and electroosmotic pumping in channel 55. Channel 57 would be surface modified, such as with linear polyacrylamide, to eliminate electroosmotic flow. Channel 55 would have a channel surface appropriate for electroosmotic flow such as native glass and be of a length to generate the desired pressure at the lower junction (or intersection). The separation channel 51, could have any appropriate surface for achieving the desired separation characteristics.

The dimensions of the various channels must be properly designed to achieve the desired flow characteristics. For example, the pressure generated by electrokinetic flow in channel 55 depends on its length and cross section. The flow due to this induced pressure at the lower intersection is split among channel 57 and the two directions for channel 51. For the majority of the flow to proceed out the channel opening, the pressure drop along this direction must be minimized compared to channel 57 and the upper portion of channel 51.

As an example of the potential distribution that might be utilized for native glass surfaces for all channels but channel 57, the upper reservoirs would have voltages to generate a high positive potential at the upper intersection. Reservoir 56 would also be at a high positive potential; reservoir 58 would be at a low potential relative to reservoir 56 and the upper intersection. The electrospray target electrode would have a potential that is more negative than reservoir 58 to produce cations or more positive to produce anions from the electrospray. Different potential distributions would be needed for the analysis of cations or anions with no electroosmotic flow in the separation channel.

An electrospray target electrode 60 is shown spaced from the exit orifice 62. In some applications, the electrode 60 is spaced 2–5 mm from the orifice 62. The electrode can have any suitable structure or shape, depending on the intended use of the electrospray. Also, while FIG. 12 shows the electrode grounded, any suitable potential can be applied to the electrode, depending on the material being sprayed and the potential present at the reservoirs.

Electroosmotically generated pressures for fluidic movement have applications beyond the electrospray technique. For example it may be desirable to have a field free region in which a chemical reaction can occur to eliminate dispersive effects from differential electrophoretic mobilities of reagents and products. Post-column labeling of biopolymers separated by electrophoresis is a specific problem where such a capability could be used. Amino acids and peptides are commonly labeled with o-phthaldialdehyde to render them detectable by fluorescence methods. A post-column reactor microchip design using purely electrokinetic pumping has been demonstrated previously in our laboratory. In this design the reaction channel of the device has a high electric field which causes band broadening due to the reaction kinetics and differential mobility between products and free amino acids.

A design similar to the sheath electrospray chip could be used for field free post-column reaction experiments. With reference to FIG. 12, channel 51 would be used for performing a separation by electrophoresis or chromatography while channel 55 would contain a buffer with the reacting species such as o-phthaldialdehyde. Channel 57 would be used in an identical mode as the previous side arm experiments to provide a means for electrical connection with minimal electroosmotic flow, thus generating a pressure at the intersection. Fluid will be forced through the portion of channel 51 below the lower intersection and contain a mixture of analyte from channel 51 and reactant from channel 55. This lower portion of the channel 51 will be field-free and thus free of axial distortion effects mentioned above. Other such applications that require pumping of fluids without the presence of electric fields could also be accommodated by such a method.

Another use of electroosmotic induced pressure is to counterbalance electrophoretic motion to obtain ultrahigh resolution separations. The resolution in an electrophoretic separation is given by R, $$R = (\mu_a - \mu_b) \sqrt{\frac{V}{32D(\mu_{avg} + \mu_{flow}}} \qquad 6)$$

where V is the applied voltage and $\mu_I$ is the electrophoretic mobility of ions a, b, the average electrophoretic mobility of the two ions and the electroosmotic flow mobility respectively. If the fluid flow in the separation channel is made to be equal and opposite to the average ion mobility, then the resolution goes to infinity under ideal conditions. Jorgenson et al. have utilized this phenomenon to achieve exceedingly high resolution using a conventional capillary and a pressure source to produce an average buffer flow equal and opposite to the ion mobility. The apparatus of Jorgenson requires an external pressure source that is switched on and off at appropriate intervals or is regulated to counterbalance ion mobility.

Figure 13:
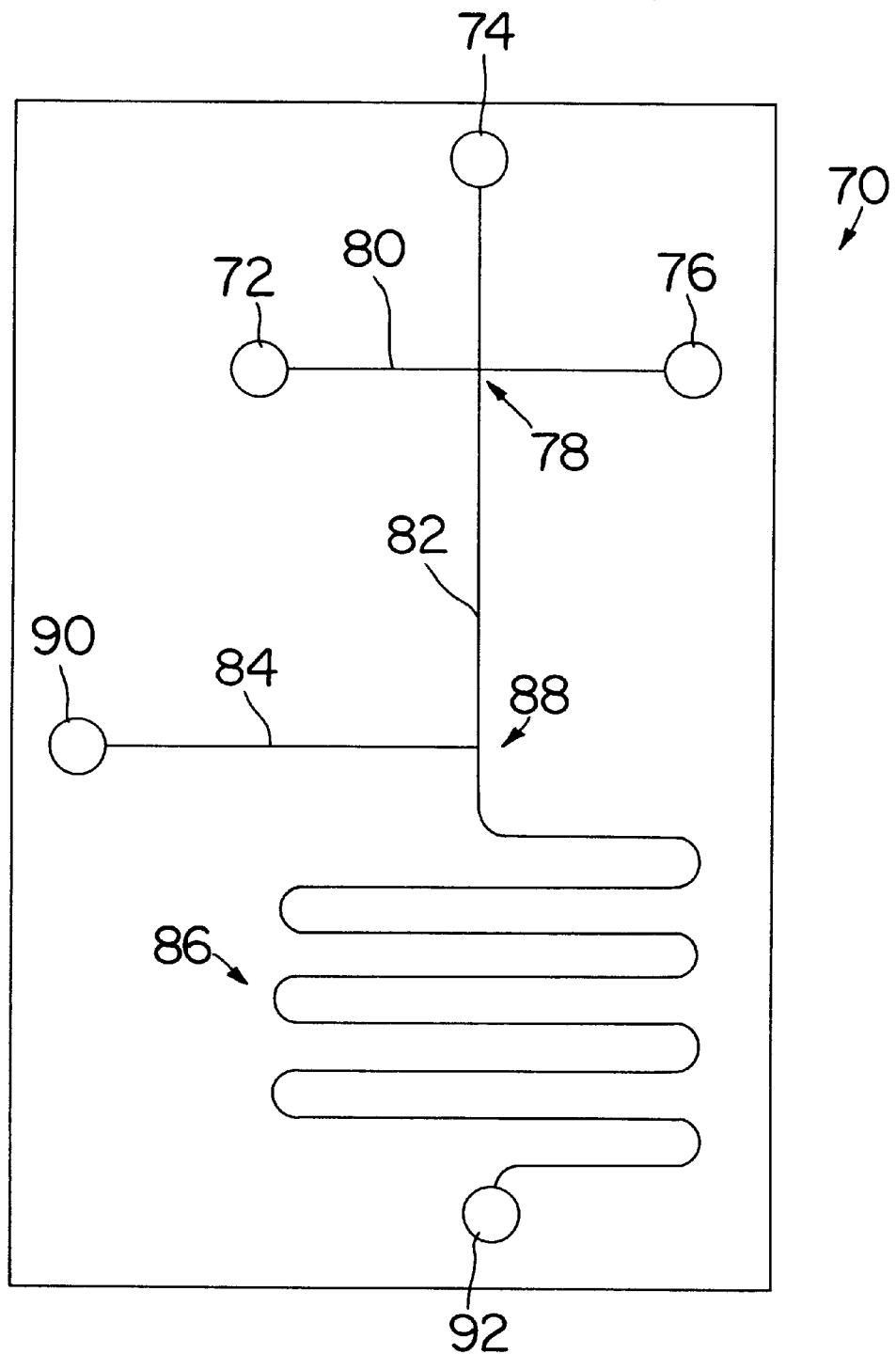
FIG. 13 is a top view of another channel architecture of a microchip used for performing high resolution separations.

The ability to generate pressures using electroosmotic pumping as described above using a side arm channel that has minimal electroosmotic flow can also be utilized to generate the counterbalancing flow for these high resolution separations. FIG. 13 shows a top view of a microchip 70 that could perform the pressure counterbalanced electrophoretic separations described here.

The upper three reservoirs 72, 74, and 76, along with the intersection 78 of channels 80 and 82 are used to make injections into separation channel 82. Channel 84 is the side arm channel similar to what has been described above. This channel, potentially along with channel 82, is modified to have minimal electroosmotic flow. Channel 86, a continuum of channel 82, has interfacial characteristics to provide high electroosmotic mobility such as native glass or silica surfaces. Channel 82, 84, and 86 meet at intersection 88.

Under normal conditions for separation of cations (assuming electroosmotic flow is minimal in channels 82 and 84), reservoir 90 would be at the lowest electric potential and reservoir 92 and intersection 78 would be at a high electric potential. The magnitude of the potential at reservoir 92 would be such that sufficient pressure would be generated at intersection 88 to produce a flow in channel 82 that opposes the mobility of the ions to be separated.

The dimensions of the various channels in FIG. 13 have to be appropriately designed to achieve the proper flow characteristics and to stay within the allowable electric field strengths for the device. For example, the flow induced by the pressure generated in channel 86 is split between channels 82 and 84; thus, there is a desire to make channel 84 longer than channel 82 to provide more flow to channel 82. The pressure generated in channel 86 is proportional to the voltage drop across this channel but the voltage is divided between channels 84 and 86; thus, it is desirable to have channel 86 longer than channel 84. The depths of the various channels relative to each other is another variable that can be manipulated in design of a structure.

While the preferred embodiment of the present invention has been shown and described, it will be understood that it is intended to cover all modifications and alternate methods falling within the spirit and scope of the invention as defined in the appended claims or their equivalents.

What is claimed is:

1. A microchip apparatus comprising:

a substrate having a microchannel formed therein said microchannel having first and second ends, and including a separation segment, a first reservoir connected to one end of the microchannel, a crosschannel forming an intersection with the microchannel, a second reservoir connected to one end of the cross channel, and a third reservoir connected to the opposite end of the cross channel, a fourth reservoir connected to the other end of the microchannel, a sidearm segment forming a confluence at one end with the microchannel at a point spaced from the intersection, and a fifth reservoir connected to the end of the sidearm segment opposite the confluence;

means for inducing electroosmotic flow of buffer introduced into the separation segment in one direction; and means for inducing electrophoretic migration of a sample introduced into the separation segment in an opposite direction.

2. A microchip according to claim 1 wherein the means for inducing electroosmotic flow includes means for establishing an electrical potential difference between the fifth reservoir and the fourth reservoir.

3. A microchip according to claim 1, wherein the means for inducing electrophoretic migration of sample includes means for establishing an electric potential between the confluence and the intersection.

4. A microchannel according to claim 3, wherein the means for establishing an electrical potential includes a voltage source, a first electrode disposed in the fourth reservoir, and a second electrode disposed in one of the first reservoir, the second reservoir, and the third reservoir.

5. A method according to claim 1, wherein the step of inducing electrophoretic migration of sample comprises establishing an electric potential between two points along. the separation segment.

6. A microchip according to claim 1, wherein at least a portion of said microchannel has a surface imparting high electroosmotic mobility.

7. A microchip according to claim 6, wherein said surface comprises glass.

8. A microchip according to claim 6, wherein said surface comprises silica.

9. A method of performing high resolution separation of a sample in a microchip comprising the steps of:

providing a microchip comprising a substrate having a microchannel formed therein, said microchannel having first and second ends and including a separation segment, a first reservoir connected to one end of the microchannel, a cross channel forming an intersection with the microchannel, a second reservoir connected to one end of the cross channel, and a third reservoir connected to the opposite end of the cross channel, a fourth reservoir connected to the other end of the microchannel, a sidearm segment forming a confluence at one end with the microchannel at a point spaced from the intersection, and a fifth reservoir connected to the end of the sidearm segment opposite the confluence;

introducing a quantity of a sample into the separation segment of the microchannel;

introducing a quantity of buffer into the separation segment of the microchannel;

inducing electroploretic migration of the sample in the separation segment in one direction; and inducing electroosmotic flow of buffer in the separation segment in the opposite direction, by establishing an electrical potential difference between the fourth reservoir and the fifth reservoir.

10. A method according to claim 5, wherein one of said two points is said intersection and the other of said two points is said confluence.

* * * * *